US012569487B2

(12) United States Patent
Fensome et al.

(10) Patent No.: US 12,569,487 B2
(45) Date of Patent: Mar. 10, 2026

(54) TREATMENT OF HIDRADENITIS WITH JAK INHIBITORS

(71) Applicant: PFIZER INC., New York, NY (US)

(72) Inventors: Andrew Fensome, Cambridge, MA (US); Brian Stephen Gerstenberger, Cambridge, MA (US); Dafydd Rhys Owen, Cambridge, MA (US)

(73) Assignee: PFIZER INC., New York, NY (US)

( * ) Notice: Subject to any disclaimer, the term of this patent is extended or adjusted under 35 U.S.C. 154(b) by 1028 days.

(21) Appl. No.: 17/641,127

(22) PCT Filed: Sep. 8, 2020

(86) PCT No.: PCT/IB2020/058333
§ 371 (c)(1),
(2) Date: Mar. 8, 2022

(87) PCT Pub. No.: WO2021/048736
PCT Pub. Date: Mar. 18, 2021

(65) Prior Publication Data
US 2025/0032492 A1     Jan. 30, 2025

Related U.S. Application Data

(60) Provisional application No. 62/899,133, filed on Sep. 11, 2019.

(51) Int. Cl.
| | |
|---|---|
| *A61K 31/519* | (2006.01) |
| *A61K 31/4985* | (2006.01) |
| *A61K 31/506* | (2006.01) |
| *A61P 17/00* | (2006.01) |

(52) U.S. Cl.
CPC ........ *A61K 31/519* (2013.01); *A61K 31/4985* (2013.01); *A61K 31/506* (2013.01); *A61P 17/00* (2018.01)

(58) Field of Classification Search
CPC .............. A61K 31/519; A61K 31/4985; A61K 31/506; A61P 17/00
See application file for complete search history.

(56) References Cited

U.S. PATENT DOCUMENTS

| | | | |
|---|---|---|---|
| 9,035,074 B2 * | 5/2015 | Brown ..................... | A61P 27/02 |
| | | | 548/565 |
| 9,549,929 B2 | 1/2017 | Brown et al. | |
| 9,663,526 B2 * | 5/2017 | Fensome ................... | A61P 1/16 |
| 10,144,738 B2 * | 12/2018 | Brown .................... | A61P 17/00 |
| 11,304,949 B2 * | 4/2022 | Howell ................... | A61K 45/06 |
| 2017/0240552 A1 | 8/2017 | Brown et al. | |
| 2019/0328739 A1 | 10/2019 | Howell et al. | |
| 2020/0399281 A1 | 12/2020 | Brown et al. | |
| 2021/0179704 A1 | 6/2021 | Giamarellos-Bourboulis et al. | |
| 2021/0377495 A1 | 12/2021 | Fensome et al. | |

FOREIGN PATENT DOCUMENTS

| | | | | |
|---|---|---|---|---|
| CN | 105008362 A | 10/2015 | | |
| CN | 107074867 A | 8/2017 | | |
| CN | 109071546 A | 12/2018 | | |
| JP | 2016-509049 A | 3/2016 | | |
| JP | 2017-524022 A | 8/2017 | | |
| JP | 2019-510003 A | 4/2019 | | |
| MX | 2020010322 A | 11/2022 | | |
| RU | 2016110852 A | 10/2017 | | |
| WO | 2012022681 A2 | 2/2012 | | |
| WO | 2014/128591 A1 | 8/2014 | | |
| WO | 2016/027195 A1 | 2/2016 | | |
| WO | 2017144995 A1 | 8/2017 | | |
| WO | WO-2017143014 A1 * | 8/2017 | .......... | A61K 31/519 |
| WO | 2018071794 A1 | 4/2018 | | |
| WO | 2019/090143 A1 | 5/2019 | | |
| WO | 2019/191679 A1 | 10/2019 | | |
| WO | 2019/191684 A1 | 10/2019 | | |
| WO | 2021048736 A1 | 3/2021 | | |

OTHER PUBLICATIONS

Shi Yu Derek Lim, et al. Systematic review of immunomodulatory therapies for hidradenitis suppurativa. Biologics: Targets and Therapy, vol. 13, pp. 53-78, published on May 1, 2019; doi: 10.2147/BTT. S199862.

International Search Report dated Nov. 12, 2020 from International Patent Application No. PCT/IB2020/058222, 5 pages.

Written Opinion dated Nov. 12, 2020 from International Patent Application No. PCT/IB2020/058222, 6 pages.

Damsky et al.; "JAK Inhibitors in Dermatology: The Promise of a New Drug Class"; J. Am ACAD Dermatol, vol. 76, No. 4, Jan. 28, 2017, pp. 736-744.

Fensome et al.; Dual Inhibition of TYK2 and jAK1 for the Treatment of Autoimmune Diseases: Discovery of ((S)-2,2-Difluorocyclopropyl)((1R,5S)-3-(2-((1-methyl-1H-pyrazol-4-yl)amino)pyrimidin-4-yl)-3,8-diazabicyclo[3.2.1]octan-8-yl) methanone (PF-06700841), Journal of Medicinal Chemistry, Aug. 16, 2018, pp. 8597-8612.

He et al.; Selective Tyk2 Inhibitors as Potential Therapeutic Agents: A Patent Review (2015-2018), Expert Opinion on Therapeutic Patents, 2019, vol. 29, No. 2, Feb. 24, 2019, pp. 137-149.

Lim et al.; "Systematic Review of Immunomodulatory Therapies for Hidradenitis Suppurativa"; Biologics: Targets and Therapy, 2019, pp. 53-78.

Solimani et al.; "Emerging Topical and Systemic JAK Inhibitors in Dermatology"; Frontiers in Immunoogy, vol. 10, Dec. 3, 2019, pp. 1-18.

International Preliminary Report on Patentability for corresponding international (PCT) application No. PCT/IB2020/058333, 8 pages, dated Mar. 24, 2022.

Japanese Office Action for corresponding Japanese application No. 2020-151758, 7 pages, dated Jun. 14, 2022.

(Continued)

*Primary Examiner* — Kevin E Weddington
(74) *Attorney, Agent, or Firm* — Lisa Mueller; Tristan A. Fuierer; Casimir Jones SC

(57) ABSTRACT

There are methods for treating hidradenitis suppurtiva using compounds and analogues that inhibit certain kinases, including Janus Kinase (JAK).

18 Claims, No Drawings

(56)           References Cited

OTHER PUBLICATIONS

Singapore Office Action for corresponding Singapore patent application No. 11202202328S, 12 pages, dated Apr. 18, 2023.

Frew, J. W. et al., "Topical, systemic and biologic therapies in hidradenitis suppurativa: pathogenic insights by examining therapeutic mechanisms" Therapeutic Advances in Chronic Disease, Mar. 1, 2019, vol. 10, pp. 1-24. Sage Publications.

Taiwan Office Action for corresponding Taiwan patent application No. 109131138 9 pages, dated Mar. 23, 2023.

Block J.L. "Hidradenitis Suppurativa From Pathogenesis to Emerging Treatment Strategies", University of Groningen, 2015.

Russian Office Action for corresponding Russian patent application No. 2022106409, 14 pages, dated May 4, 2023.

Russian Search Report for corresponding Russian patent application No. 2022106409, 6 pages, dated May 4, 2023.

Written Opinion for International (PCT) application No. PCT/US/23/63938, 5 pages, dated Jun. 21, 2023.

International Search Report for International (PCT) application No. PCT/US/23/63938, 3 pages, dated Jun. 21, 2023.

Thorlacius, L., et al., "A core domain set for hidradenitis suppurativa trial outcomes: an international Delphi process*" British Journal of Dermatology, 179(3), pp. 642-650 (2018), Wiley & Sons.

Kimball, A., et al., "Two Phase 3 Trials of Adalimumab for Hidradenitis Suppurativa", New England Journal of Medicine , 375(5), pp. 422-434 (Aug. 4, 2016), Massachusetts Medical Society.

Jemec, G.B., "Hidradenitis Suppurativa", New England Journal of Medicine, 366: 158-64 (Jan. 12, 2012), Massachusetts Medical Society.

Zouboulis, C., et al., "Hidradenitis Suppurativa/Acne Inversa: Criteria for Diagnosis, Severity Assessment, Classification and Disease Evaluation", Dermatology, 231(2), pp. 184-190 (2015), Karger.

Yamaoka et al. "The Janus kinases (Jaks)" Genome Biology, Nov. 30, 2004, 253 (5), BioMed Central Ltd.

Kisseleva et al., "Signaling through the JAK/STAT Pathway, Recent Advances and Future Challenges" Gene, 2002, (285), pp. 1-24; Elsevier.

Ross, Y. et al. Association of hidradenitis suppurativa with autoimmune disease and autoantibodies. Rheumatol Adv Pract. Dec. 27, 2021;6(2):rkab108 (Year: 2021).

Alavi, A. et al. Janus kinase 1 inhibitor INCB054707 for patients with moderate-to-severe hidradenitis suppurative: results from two phase II studies. Br J Dermatol. Mar. 6, 2022;186(5):803-813 (Year: 2022).

Williamson, D. Descriptive epidemiology of body weight and weight change in u.s. adults. Annals of Internal Medicine, 1993, 119, 7, 646-649 (Year: 1993).

* cited by examiner

TREATMENT OF HIDRADENITIS WITH JAK INHIBITORS

FIELD OF THE INVENTION

The present invention provides methods for treating hidradenitis suppurtiva using compounds and analogues which inhibit certain kinases including Janus Kinase (JAK).

BACKGROUND OF THE INVENTION

Protein kinases are families of enzymes that catalyze the phosphorylation of specific residues in proteins, broadly classified into tyrosine and serine/threonine kinases. Inappropriate kinase activity, arising from mutation, over-expression, or inappropriate regulation, dys-regulation or de-regulation, as well as over- or under-production of growth factors or cytokines has been implicated in many diseases, including but not limited to cancer, cardiovascular diseases, allergies, asthma and other respiratory diseases, autoimmune diseases, inflammatory diseases, bone diseases, metabolic disorders, and neurological and neurodegenerative disorders such as Alzheimer's disease. Inappropriate kinase activity triggers a variety of biological cellular responses relating to cell growth, cell differentiation, cell function, survival, apoptosis, and cell mobility implicated in the aforementioned and related diseases.

Thus, protein kinases have emerged as an important class of enzymes as targets for therapeutic intervention. In particular, the JAK family of cellular protein tyrosine kinases (JAK1, JAK2, JAK3, and Tyk2) play a central role in cytokine signaling (Kisseleva et al., *Gene,* 2002, 285, 1; Yamaoka et al. *Genome Biology* 2004, 5, 253). Upon binding to their receptors, cytokines activate JAK which then phosphorylate the cytokine receptor, thereby creating docking sites for signaling molecules, notably, members of the signal transducer and activator of transcription (STAT) family that ultimately lead to gene expression. Numerous cytokines are known to activate the JAK family. These cytokines include, the interferon (IFN) family (IFN-alpha, IFN-beta, IFN-omega, Limitin, IFN-gamma, IL-10, IL-19, IL-20, IL-22), the gp130 family (IL-6, IL-11, OSM, LIF, CNTF, NNT-1/BSF-3, G-CSF, CT-1, Leptin, IL-12, IL-23), gamma C family (IL-2, IL-7, TSLP, IL-9, IL-15, IL-21, IL-4, IL-13), IL-3 family (IL-3, IL-5, GM-CSF), single chain family (EPO, GH, PRL, TPO), receptor tyrosine kinases (EGF, PDGF, CSF-1, HGF), and G-protein coupled receptors (AT1).

Hidradenitis suppurativa (HS) is a chronic, inflammatory, recurrent, debilitating skin disease that usually presents after puberty with painful, deep-seated, inflamed lesions in the apocrine gland-bearing areas of the body. Zouboulis, C., et al., *Dermatology,* 231 (2), pp. 184-190 (2015). HS presents a variable clinical course. One of the main features of the disease is the intertriginous occurrence, although, other areas of skin may also be affected. The affected areas are in decreasing order of frequency: inguinal, axillary, perineal and perianal as well as the submammary and/or intermammary fold in women, buttocks, mons pubis, scalp, area behind the ears and eyelids.

The prevalence of self-reported disease is about 1% in Western Europe. The average interval from the onset of symptoms to diagnosis is 7.2 years. Women are affected 2 to 5 times as frequently as men, and the disease may be more common in blacks than in whites. Disease severity ranges from mild (localized lesions) to severe (multiple areas of widely dispersed lesions, including interconnected sinus tracts and hypertrophic scars). Pain, drainage, and range of motion limitations from scarring can decrease the quality of life. Jemec, G. B., *New Eng. J. Med.,* 366:158-64 (2012); Kimball, A., et al., *New Eng. J. Med.,* 375 (5), pp. 422-434 (2016).

Pain is a prominent feature of HS, which is reflected in the recently defined set of core outcomes to be assessed in future trials. Thorlacius, L., et al., *Brit. J. Derm.,* 179 (3), pp. 642-650 (2018). The majority of patients rated their pain on a Numerical Rating Scale-11 (NRS 11) ranging from 4/10-10/10 and described it at various times as hot, burning, pressure stretching, cutting, sharp, taut, splitting, gnawing, pressing sore, throbbing, and aching. Currently adalimumab is the only approved medical treatment for moderate to severe HS. It is based on two similarly designed (PIONEER I and PIONEER II), Phase 3 multicenter trials of adalimumab for HS. Kimball, A., et al., *New Eng. J. Med.,* 375 (5), pp. 422-434 (2016). A total of 307 patients were enrolled in PIONEER I, and 326 were enrolled in PIONEER II. Clinical response rates [hidradenitis suppurativa clinical response (HiSCR)]: defined as at least a 50% reduction from baseline in the abscess and inflammatory nodule count, with no increase in abscess or draining fistula counts] at Week 12 were significantly higher for the groups receiving adalimumab weekly than for the placebo groups: 41.8% versus 26.0% in PIONEER I (P=0.003) and 58.9% versus 27.6% in PIONEER II (P<0.001). Patients receiving adalimumab had significantly greater improvement than the placebo groups in rank-ordered secondary outcomes (lesions, pain, and the modified Sartorius score for disease severity) at Week 12 in PIONEER II only. Kimball, A., et al., ibid. The main difference between the study designs is that in PIONEER I, patients receiving oral antibiotic agents for HS were required to stop treatment for at least 28 days before baseline; in PIONEER II, patients were allowed to continue treatment with antibiotics (tetracycline class) in stable doses.

Thus, a significant number of patients (~40%) with moderate to severe HS did not respond to treatment with adalimumab, and therefore there is still an unmet need for an effective, safe, and well tolerated treatment in patients with moderate to severe HS. Disclosed herein is the discovery that compounds and analogues which inhibit certain kinases such as JAK1, Tyk2/JAK1, and Tyk2 are useful for treating HS. Accordingly, described herein are methods of reducing the severity of HS symptoms in a human subject. These methods can include the step of administering to the subject a pharmaceutical composition comprising such compounds are effective to reduce the number and/or size of inflammatory lesions (e.g., nodule. abscesses. or draining fistulas), prevent their progression, reduce the pain caused thereby, or delay further lesion development.

SUMMARY OF THE INVENTION

The present invention provides a method for treating hidradenitis suppurtiva in a subject, the method comprising administering to the subject in need thereof any of the compounds disclosed herein which inhibit JAK such as JAK1, Tyk2/JAK1, and Tyk2.

In some embodiments, the invention provides a method for treating hidradenitis suppurtiva in a subject, the method comprising administering to the subject in need thereof, N-{cis-3-[methyl(7H-pyrrolo[2,3-d]pyrimidin-4-yl)amino] cyclobutyl}-propane-1-sulfonamide or a pharmaceutical salt thereof.

In a further aspect the invention provides a method for treating hidradenitis suppurtiva in a subject, the method comprising administering to the subject in need thereof, N-{cis-3-[methyl(7H-pyrrolo[2,3-d]pyrimidin-4-yl)amino]cyclobutyl}-propane-1-sulfonamide at a dose of 0.01 to about 100 mg/kg of body weight/day.

In some embodiments, the invention provides a method for treating hidradenitis suppurtiva in a subject, the method comprising administering to the subject in need thereof, [(1S)-2,2-difluorocyclo-propyl][(1R,5S)-3-{2-[(1-methyl-1H-pyrazol-4-yl)amino]pyrimidin-4-yl}-3,8-diazabicyclo-[3.2.1]oct-8-yl]methanone or a pharmaceutical salt thereof.

In a further aspect the invention provides a method for treating hidradenitis suppurtiva in a subject, the method comprising administering to the subject in need thereof, [(1S)-2,2-difluorocyclo-propyl][(1R,5S)-3-{2-[(1-methyl-1H-pyrazol-4-yl)amino]pyrimidin-4-yl}-3,8-diazabicyclo-[3.2.1]oct-8-yl]methanone at a dose of 0.01 to about 100 mg/kg of body weight/day.

In some embodiments, the invention provides a method for treating hidradenitis suppurtiva in a subject, the method comprising administering to the subject in need thereof, (1r,3r)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile or a pharmaceutical salt thereof.

In a further aspect the invention provides a method for treating hidradenitis suppurtiva in a subject, the method comprising administering to the subject in need thereof, (1r,3r)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile at a dose of 0.01 to about 100 mg/kg of body weight/day.

Clinical benefit of the treatment according to the invention can be measured, for example by hidradenitis suppurtiva clinical response score (HiSCR).

In some embodiments, the JAK inhibitor effectively improves the HiSCR scores.

Also provided is the use of a JAK inhibitor in the manufacture of a medicament for use in a method of treating and preventing hidradenitis suppurtiva in a subject, as described herein.

The present invention will be further understood from the following description given by way of example only. While the present invention is not so limited, an appreciation of various aspects of the invention will be gained through the following discussion and the examples.

As used herein, "subject" refers to mammals, companion animals or livestock animals.

The term "companion animal" or "companion animals" refers to animals kept as pets or household animal. Examples of companion animals include dogs, cats, and rodents including hamsters, guinea pigs, gerbils and the like, rabbits, ferrets and birds.

The term "livestock" refers to animals reared or raised in an agricultural setting to make products such as food or fiber, or for its labor. In some embodiments, livestock are suitable for consumption by mammals, for example humans. Examples of livestock animals include cattle, goats, horses, pigs, sheep, including lambs, and rabbits, as well as birds, such as chickens, ducks and turkeys.

The term "treating" or "treatment" means an alleviation of symptoms associated with a disease, disorder or condition, or halt of further progression or worsening of those symptoms. Depending on the disease and condition of the patient, the term "treatment" as used herein may include one or more of curative, palliative and prophylactic treatment. Treatment can also include administering a pharmaceutical formulation of the present invention in combination with other therapies.

The term "therapeutically-effective" indicates the capability of an agent to prevent, or improve the severity of, the disorder, while avoiding adverse side effects typically associated with alternative therapies. The phrase "therapeutically-effective" is to be understood to be equivalent to the phrase "effective for the treatment, prevention, or amelioration", and both are intended to qualify the amount of each agent for use in the combination therapy which will achieve the goal of improvement in the severity of disease, or pain or other symptom thereof, and the frequency of incidence over treatment of each agent by itself, while avoiding adverse side effects typically associated with alternative therapies.

"Pharmaceutically acceptable" means suitable for use in a "subject."

DETAILED DESCRIPTION OF THE INVENTION

The present invention is related to a method for treating hidradenitis suppurtiva in a subject, the method comprising administering to the subject in need thereof compounds which inhibit certain JAK, such as JAK1, Tyk2/JAK1, and Tyk2. The present invention further provides pharmaceutical compositions comprising such inhibitors. Accordingly, the present invention provides a method for treating hidradenitis suppurtiva in a subject having lesions associated with hidradenitis suppurativa, the method comprising the step of administering to the subject in need thereof a compound selected from the group consisting of:

[(1S)-2,2-difluorocyclopropyl]{(1R,5S)-3-[2-({5-fluoro-6-[(3S)-3-hydroxypyrrolidin-1-yl]pyridin-3-yl}amino)pyrimidin-4-yl]-3,8-diazabicyclo[3.2.1]oct-8-yl}methanone;

(1R,5S)—N-ethyl-3-[2-(1,2-thiazol-4-ylamino)pyrimidin-4-yl]-3,8-diazabicyclo[3.2.1]octane-8-carboxamide;

4-{(1R,5S)-8-[(2,2-difluorocyclopropyl)methyl]-3,8-diazabicyclo[3.2.1]oct-3-yl}-N-(1H-pyrazol-4-yl)pyrimidin-2-amine;

(1R,5S)-3-(2-{[5-chloro-6-(methylcarbamoyl)pyridin-3-yl]amino}pyrimidin-4-yl)-N-ethyl-3,8-diazabicyclo[3.2.1]octane-8-carboxamide;

cyclopropyl[(1R,5S)-3-(2-{[1-(2-hydroxyethyl)-1H-pyrazol-4-yl]amino}pyrimidin-4-yl)-3,8-diazabicyclo[3.2.1]oct-8-yl]methanone;

N-(1-methyl-1H-pyrazol-4-yl)-4-{(1R,5S)-8-[1-(methylsulfonyl)azetidin-3-yl]-3,8-diazabicyclo[3.2.1]oct-3-yl}pyrimidin-2-amine;

4-({4-[(1R,5S)-8-{[(1S)-2,2-difluorocyclopropyl]carbonyl}-3,8-diazabicyclo[3.2.1]oct-3-yl]pyrimidin-2-yl}amino)-N,6-dimethylpyridine-2-carboxamide;

5-({4-[(1R,5S)-8-{[(1R,2S)-2-fluorocyclopropyl]carbonyl}-3,8-diazabicyclo[3.2.1]oct-3-yl]pyrimidin-2-yl}amino)-N,3-dimethylpyridine-2-carboxamide;

cyclopropyl[(1R,5S)-3-{2-[(1-methyl-1H-pyrazol-4-yl)amino]pyrimidin-4-yl}-3,8-diazabicyclo[3.2.1]oct-8-yl]methanone;

3-{(1R,5S)-3-[2-(1H-pyrazol-4-ylamino)pyrimidin-4-yl]-3,8-diazabicyclo[3.2.1]oct-8-yl}butanenitrile;

5-({4-[(1R,5S)-8-(cyclopropylcarbonyl)-3,8-diazabicyclo[3.2.1]oct-3-yl]pyrimidin-2-yl}amino)-N-ethyl-3-methylpyridine-2-carboxamide;

3-[(1R,5S)-3-{2-[(1-methyl-1H-pyrazol-4-yl)amino]pyrimidin-4-yl}-3,8-diazabicyclo[3.2.1]oct-8-yl]butanenitrile;

5-({4-[(1R,5S)-8-(cyclopropylcarbonyl)-3,8-diazabicyclo[3.2.1]oct-3-yl]pyrimidin-2-yl}amino)-3-methylpyridine-2-carboxamide;

(1R,5S)—N-ethyl-3-(2-{[5-fluoro-6-(methylcarbamoyl)pyridin-3-yl]amino}pyrimidin-4-yl)-3,8-diazabicyclo[3.2.1]octane-8-carboxamide;

3-chloro-5-({4-[(1R,5S)-8-(cyclopropylcarbonyl)-3,8-diazabicyclo[3.2.1]oct-3-yl]pyrimidin-2-yl}amino)-N-methylpyridine-2-carboxamide;

(1R,5S)-3-{2-[(1-methyl-1H-pyrazol-4-yl)amino]pyrimidin-4-yl}-N-(propan-2-yl)-3,8-diazabicyclo[3.2.1]octane-8-carboxamide;

(3,3-difluorocyclobutyl)[(1R,5S)-3-{2-[(1-methyl-1H-pyrazol-4-yl)amino]pyrimidin-4-yl}-3,8-diazabicyclo[3.2.1]oct-8-yl]methanone;

1-({(1R,5S)-3-[2-(1H-pyrazol-4-ylamino)pyrimidin-4-yl]-3,8-diazabicyclo[3.2.1]oct-8-yl}methyl)cyclopropanecarbonitrile;

3-[(1R,5S)-3-{2-[(1-methyl-1H-pyrazol-4-yl)amino]pyrimidin-4-yl}-3,8-diazabicyclo[3.2.1]oct-8-yl]butanenitrile;

(1S,2R)-2-{[(1R,5S)-3-{2-[(1-methyl-1H-pyrazol-4-yl)amino]pyrimidin-4-yl}-3,8-diazabicyclo[3.2.1]oct-8-yl]carbonyl}cyclopropanecarbonitrile;

(1R,2S)-2-{[(1R,5S)-3-{2-[(1-methyl-1H-pyrazol-4-yl)amino]pyrimidin-4-yl}-3,8-diazabicyclo[3.2.1]oct-8-yl]carbonyl}cyclopropanecarbonitrile;

[(1R,2R)-2-fluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone;

[(1R,2R)-2-fluorocyclopropyl][(1R,5S)-3-{2-[(1-methyl-1H-pyrazol-4-yl)amino]pyrimidin-4-yl}-3,8-diazabicyclo[3.2.1]oct-8-yl]methanone;

(1R,5S)-3-{2-[(1-methyl-1H-pyrazol-4-yl)amino]pyrimidin-4-yl}-3,8-diazabicyclo[3.2.1]octane-8-carboxamide;

(1R,5S)-3-{2-[(1-methyl-1H-pyrazol-4-yl)amino]pyrimidin-4-yl}-N-[5-(trifluoromethyl)pyridin-2-yl]-3,8-diazabicyclo[3.2.1]octane-8-carboxamide;

N,3-dimethyl-5-[(4-{(1R,5S)-8-[(3-methyloxetan-3-yl)methyl]-3,8-diazabicyclo[3.2.1]oct-3-yl}pyrimidin-2-yl)amino]pyridine-2-carboxamide;

{3-[(1R,5S)-3-{2-[(1-methyl-1H-pyrazol-4-yl)amino]pyrimidin-4-yl}-3,8-diazabicyclo[3.2.1]oct-8-yl]-1-(methylsulfonyl)azetidin-3-yl}acetonitrile;

4-({4-[8-(cyanoacetyl)-3,8-diazabicyclo[3.2.1]oct-3-yl]pyrimidin-2-yl}amino)-N-ethylbenzamide;

(1R,5S)—N-(cyanomethyl)-3-{2-[(1-methyl-1H-pyrazol-4-yl)amino]pyrimidin-4-yl}-3,8-diazabicyclo[3.2.1]octane-8-carboxamide;

5-({4-[(1R,5S)-8-{[(1S,2R)-2-fluorocyclopropyl]carbonyl}-3,8-diazabicyclo[3.2.1]oct-3-yl]pyrimidin-2-yl}amino)-N,3-dimethylpyridine-2-carboxamide;

5-({4-[(1R,5S)-8-(cis-3-cyanocyclobutyl)-3,8-diazabicyclo[3.2.1]oct-3-yl]pyrimidin-2-yl}amino)-N,3-dimethylpyridine-2-carboxamide;

5-({4-[(1R,5S)-8-{[(1R)-2,2-difluorocyclopropyl]methyl}-3,8-diazabicyclo[3.2.1]oct-3-yl]pyrimidin-2-yl}amino)-N,3-dimethylpyridine-2-carboxamide;

N,3-dimethyl-5-({4-[(1R,5S)-8-(1,2-oxazol-5-ylmethyl)-3,8-diazabicyclo[3.2.1]oct-3-yl]pyrimidin-2-yl}amino)pyridine-2-carboxamide;

2-[5-({4-[(1R,5S)-8-{[(1S)-2,2-difluorocyclopropyl]carbonyl}-3,8-diazabicyclo[3.2.1]oct-3-yl]pyrimidin-2-yl}amino)pyridin-2-yl]-2-methylpropanenitrile;

3-{(1R,5S)-3-[2-(1H-pyrazol-4-ylamino)pyrimidin-4-yl]-3,8-diazabicyclo[3.2.1]oct-8-yl}propanenitrile;

(1R,5S)—N-ethyl-3-[2-(1H-pyrazol-4-ylamino)pyrimidin-4-yl]-3,8-diazabicyclo[3.2.1]octane-8-carboxamide;

4-[(1R,5S)-8-{[(1S)-2,2-difluorocyclopropyl]methyl}-3,8-diazabicyclo[3.2.1]oct-3-yl]-N-(1-methyl-1H-pyrazol-4-yl)pyrimidin-2-amine;

[(1S)-2,2-difluorocyclopropyl][(1R,5S)-3-(2-{[5-fluoro-6-(2-hydroxyethyl)pyridin-3-yl]amino}pyrimidin-4-yl)-3,8-diazabicyclo[3.2.1]oct-8-yl]methanone;

[(1S)-2,2-difluorocyclopropyl][(1R,5S)-3-(2-{[5-fluoro-6-(3-hydroxyazetidin-1-yl)pyridin-3-yl]amino}pyrimidin-4-yl)-3,8-diazabicyclo[3.2.1]oct-8-yl]methanone;

[(1R,5S)-3-(2-{[5-chloro-6-(2-hydroxyethoxy)pyridin-3-yl]amino}pyrimidin-4-yl)-3,8-diazabicyclo[3.2.1]oct-8-yl][(1S)-2,2-difluorocyclopropyl]methanone;

{3-[(1R,5S)-3-{2-[(1-methyl-1H-pyrazol-4-yl)amino]pyrimidin-4-yl}-3,8-diazabicyclo[3.2.1]oct-8-yl]oxetan-3-yl}acetonitrile;

[(1R,5S)-3-(2-{[5-chloro-6-(2-hydroxyethyl)pyridin-3-yl]amino}pyrimidin-4-yl)-3,8-diazabicyclo[3.2.1]oct-8-yl][(1S)-2,2-difluorocyclopropyl]methanone;

2-[(1R,5S)-3-{2-[(1-methyl-1H-pyrazol-4-yl)amino]pyrimidin-4-yl}-3,8-diazabicyclo[3.2.1]oct-8-yl]pyridine-4-carbonitrile;

3-[(1R,5S)-3-{2-[(1-methyl-1H-pyrazol-4-yl)amino]pyrimidin-4-yl}-3,8-diazabicyclo[3.2.1]oct-8-yl]cyclobutanecarbonitrile;

2-[(1R,5S)-3-{2-[(1-methyl-1H-pyrazol-4-yl)amino]pyrimidin-4-yl}-3,8-diazabicyclo[3.2.1]oct-8-yl]-1,3-oxazole-5-carbonitrile;

(1R,5S)—N-(2-cyanoethyl)-3-{2-[(1-methyl-1H-pyrazol-4-yl)amino]pyrimidin-4-yl}-3,8-diazabicyclo[3.2.1]octane-8-carboxamide;

N-(1-methyl-1H-pyrazol-4-yl)-4-[(1R,5S)-8-(1,2-oxazol-4-ylmethyl)-3,8-diazabicyclo[3.2.1]oct-3-yl]pyrimidin-2-amine;

4-({4-[(1R,5S)-8-{[(1S)-2,2-difluorocyclopropyl]carbonyl}-3,8-diazabicyclo[3.2.1]oct-3-yl]pyrimidin-2-yl}amino)-6-(hydroxymethyl)-N-methylpyridine-2-carboxamide;

(1-fluorocyclopropyl)[(1R,5S)-3-{2-[(1-methyl-1H-pyrazol-4-yl)amino]pyrimidin-4-yl}-3,8-diazabicyclo[3.2.1]oct-8-yl]methanone;

N-(1-methyl-1H-pyrazol-4-yl)-4-[(1R,5S)-8-(1,3-thiazol-2-ylmethyl)-3,8-diazabicyclo[3.2.1]oct-3-yl]pyrimidin-2-amine;

cyclopropyl {(1R,5S)-3-[2-(1,2-thiazol-4-ylamino)pyrimidin-4-yl]-3,8-diazabicyclo[3.2.1]oct-8-yl}methanone;

[(1S)-2,2-difluorocyclopropyl]{(1R,5S)-3-[2-({5-fluoro-6-[(3R)-3-hydroxypyrrolidin-1-yl]pyridin-3-yl}amino)pyrimidin-4-yl]-3,8-diazabicyclo[3.2.1]oct-8-yl}methanone;

5-({4-[(1R,5S)-8-{[(1S)-2,2-difluorocyclopropyl]methyl}-3,8-diazabicyclo[3.2.1]oct-3-yl]pyrimidin-2-yl}amino)-N,3-dimethylpyridine-2-carboxamide;

4-[(1R,5S)-8-{[(1R)-2,2-difluorocyclopropyl]methyl}-3,8-diazabicyclo[3.2.1]oct-3-yl]-N-(1-methyl-1H-pyrazol-4-yl)pyrimidin-2-amine;

6-({4-[(1R,5S)-8-(cyclopropylcarbonyl)-3,8-diazabicyclo[3.2.1]oct-3-yl]-5-fluoropyrimidin-2-yl}amino) imidazo[1,2-a]pyridine-2-carboxamide;

5-({4-[(1R,5S)-8-(cyclopropylcarbonyl)-3,8-diazabicyclo[3.2.1]oct-3-yl]-5-fluoropyrimidin-2-yl}amino)pyridine-2-sulfonamide;

5-({4-[(1R,5S)-8-(trans-3-cyanocyclobutyl)-3,8-diazabicyclo[3.2.1]oct-3-yl]pyrimidin-2-yl}amino)-N,3-dimethylpyridine-2-carboxamide;

1,2-oxazol-5-yl {(1R,5S)-3-[2-(1H-pyrazol-4-ylamino)py-rimidin-4-yl]-3,8-diazabicyclo[3.2.1]oct-8-yl}methanone;

N-(1-methyl-1H-pyrazol-4-yl)-4-[(1R,5S)-8-(methylsulfo-nyl)-3,8-diazabicyclo[3.2.1]oct-3-yl]pyrimidin-2-amine;

(1S,2S)-2-{[(1R,5S)-3-{2-[(1-methyl-1H-pyrazol-4-yl) amino]pyrimidin-4-yl}-3,8-diazabicyclo[3.2.1]oct-8-yl] methyl}cyclopropanecarbonitrile;

3-({4-[(1R,5S)-8-(cyclopropylcarbonyl)-3,8-diazabicyclo [3.2.1]oct-3-yl]-5-fluoropyrimidin-2-yl}amino)-N-pro-pyl-1H-pyrazole-5-carboxamide;

(1S,2S)-2-{[(1R,5S)-3-{2-[(1-methyl-1H-pyrazol-4-yl) amino]pyrimidin-4-yl}-3,8-diazabicyclo[3.2.1]oct-8-yl] methyl}cyclopropanecarbonitrile;

cyclopropyl {(1R,5S)-3-[5-fluoro-2-(pyridazin-4-ylamino) pyrimidin-4-yl]-3,8-diazabicyclo[3.2.1]oct-8-yl}methanone;

4-({4-[6-(2,2-difluoropropanoyl)-3,6-diazabicyclo[3.1.1] hept-3-yl]-5-fluoropyrimidin-2-yl}amino)-N-ethyl-2-methylbenzamide;

(1S,2S)-2-cyano-N-[(1S,5R,6R)-3-(2-{[6-(2-hydroxy-ethoxy)pyridin-3-yl]amino}-5-methylpyrimidin-4-yl)-6-methyl-3-azabicyclo[3.1.0]hex-1-yl]cyclopropanecar-boxamide;

N-[(1S,5R)-3-(5-chloro-2-{[1-(2-hydroxyethyl)-1H-pyra-zol-4-yl]amino}pyrimidin-4-yl)-3-azabicyclo[3.1.0]hex-1-yl]cyclopropanecarboxamide;

(1S)-2,2-difluoro-N-[(1S,5R,6R)-3-(5-fluoro-2-{[1-(oxetan-3-yl)-1H-pyrazol-4-yl]amino}pyrimidin-4-yl)-6-methyl-3-azabicyclo[3.1.0]hex-1-yl]cyclopropanecar-boxamide;

(1S)-2,2-difluoro-N-[(1S,5S)-3-{5-fluoro-2-[(1-methyl-1H-pyrazol-4-yl)amino]pyrimidin-4-yl}-5-(hydroxymethyl)-3-azabicyclo[3.1.0]hex-1-yl]cyclopropanecarboxamide;

N-{(1S,5R,6R)-3-[5-fluoro-2-({6-[(2S)-1-hydroxypropan-2-yl]pyridin-3-yl}amino)pyrimidin-4-yl]-6-methyl-3-azabicyclo[3.1.0]hex-1-yl}cyclopropanecarboxamide;

5-[(4-{(1S,5R,6R)-1-[(cyclopropylcarbonyl)amino]-6-methyl-3-azabicyclo[3.1.0]hex-3-yl}-5-fluoropyrimidin-2-yl)amino]-N,3-dimethylpyridine-2-carboxamide;

N-{(1S,5R,6R)-3-[2-({5-chloro-6-[(1R)-1-hydroxyethyl] pyridin-3-yl}amino)-5-fluoropyrimidin-4-yl]-6-methyl-3-azabicyclo[3.1.0]hex-1-yl}cyclopropanecarboxamide;

(1R)-2,2-difluoro-N-[(1R,5S,6S)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide;

5-[(4-{(1R,5S,6S)-1-[(cyclopropylcarbonyl)amino]-6-methyl-3-azabicyclo[3.1.0]hex-3-yl}-5-fluoropyrimidin-2-yl)amino]-N,3-dimethylpyridine-2-carboxamide;

N-[(1R,5S)-3-(5-chloro-2-{[1-(2-hydroxyethyl)-1H-pyra-zol-4-yl]amino}pyrimidin-4-yl)-3-azabicyclo[3.1.0]hex-1-yl]cyclopropanecarboxamide; N-{(1S,5R,6R)-3-[5-fluoro-2-({6-[(2R)-1-hydroxypropan-2-yl]pyridin-3-yl}amino)pyrimidin-4-yl]-6-methyl-3-azabicyclo[3.1.0] hex-1-yl}cyclopropanecarboxamide; and, (1S)-2,2-difluoro-N-[(1R,5S,6S)-3-{5-fluoro-2-[(1-methyl-1H-pyrazol-4-yl)amino]pyrimidin-4-yl}-6-methyl-3-azabicyclo[3.1.0]hex-1-yl]cyclopropanecarboxamide; or, a pharmaceutically acceptable salt thereof.

The invention also provides said method, wherein said compound is [(1S)-2,2-difluorocyclo-propyl][(1R,5S)-3-{2-[(1-methyl-1H-pyrazol-4-yl)amino]pyrimidin-4-yl}-3,8-di-azabicyclo[3.2.1]oct-8-yl]methanone; or, a pharmaceuti-cally acceptable salt thereof. The invention further provides the method wherein said salt is the p-toluenesulfonic acid salt.

The invention also provides said method, wherein said compound is [(1R)-2,2-difluorocyclo-propyl][(1R,5S)-3-{2-[(1-methyl-1H-pyrazol-4-yl)amino]pyrimidin-4-yl]-3,8-di-azabicyclo[3.2.1]oct-8-yl]methanone; or, a pharmaceuti-cally acceptable salt thereof.

The invention further provides a method for treating hidradenitis suppurtiva in a subject having lesions associated with hidradenitis suppurativa, the method comprising the step of administering to the subject in need thereof, a compound selected from the group consisting of:

4-cyano-N-{cis-3-[methyl(7H-pyrrolo[2,3-d]pyrimidin-4-yl)amino]cyclobutyl}pyridine-2-sulfonamide;

2,2,2-trifluoro-N-{cis-3-[methyl(7H-pyrrolo[2,3-d]pyrimi-din-4-yl)amino]cyclobutyl}-ethanesulfonamide;

2-methyl-N-{cis-3-[methyl(7H-pyrrolo[2,3-d]pyrimidin-4-yl)amino]cyclobutyl}-propane-1-sulfonamide;

N-{cis-3-[methyl(7H-pyrrolo[2,3-d]pyrimidin-4-yl)amino] cyclobutyl}propane-1-sulfonamide;

1-cyclopropyl-N-{cis-3-[methyl(7H-pyrrolo[2,3-d]pyrimi-din-4-yl)amino]cyclobutyl}-methanesulfonamide;

N-{cis-3-[(butylsulfonyl)methyl]cyclobutyl}-N-methyl-7H-pyrrolo[2,3-d]pyrimidin-4-amine;

1-cyclopropyl-N-{cis-3-[methyl(7H-pyrrolo[2,3-d]pyrimi-din-4-yl)amino]cyclobutyl}-azetidine-3-sulfonamide;

3-cyano-N-{cis-3-[methyl(7H-pyrrolo[2,3-d]pyrimidin-4-yl)amino]cyclobutyl}-azetidine-1-sulfonamide;

(1R,5S)—N-{cis-3-[methyl(7H-pyrrolo[2,3-d]pyrimidin-4-yl)amino]cyclobutyl}-6-oxa-3-azabicyclo[3.1.1]heptane-3-sulfonamide;

(3R)-3-cyano-N-{cis-3-[methyl(7H-pyrrolo[2,3-d]pyrimi-din-4-yl)amino]cyclobutyl}-pyrrolidine-1-sulfonamide;

(3S)-3-cyano-N-{cis-3-[methyl(7H-pyrrolo[2,3-d]pyrimi-din-4-yl)amino]cyclobutyl}-pyrrolidine-1-sulfonamide;

N-{cis-3-[methyl(7H-pyrrolo[2,3-d]pyrimidin-4-yl)amino] cyclobutyl}-1-(oxetan-3-yl)methane-sulfonamide;

1-(3,3-difluorocyclobutyl)-N-{cis-3-[methyl(7H-pyrrolo[2, 3-d]pyrimidin-4-yl)amino]cyclobutyl}methane-sulfona-mide;

trans-3-(cyanomethyl)-N-{cis-3-[methyl(7H-pyrrolo[2,3-d] pyrimidin-4-yl)amino]-cyclobutyl}cyclo-butanesulfona-mide;

cis-3-(cyanomethyl)-N-{cis-3-[methyl(7H-pyrrolo[2,3-d] pyrimidin-4-yl)amino]-cyclobutyl}cyclobutane-sulfona-mide;

N-[cis-3-({[(3,3-difluorocyclobutyl)methyl] sulfonyl}methyl)cyclobutyl]-N-methyl-7H-pyrrolo[2,3-d]pyrimidin-4-amine;

(1S,5S)-1-cyano-N-{cis-3-[methyl(7H-pyrrolo[2,3-d]py-rimidin-4-yl)amino]cyclobutyl}-3-azabicyclo[3.1.0] hexane-3-sulfonamide;

(1R,5S)-1-cyano-N-{cis-3-[methyl(7H-pyrrolo[2,3-d]py-rimidin-4-yl)amino]cyclobutyl}-3-azabicyclo[3.1.0] hexane-3-sulfonamide;

(3R)-1-[({cis-3-[methyl(7H-pyrrolo[2,3-d]pyrimidin-4-yl) amino]cyclobutyl}meth-yl)sulfonyl]pyrrolidine-3-carbo-nitrile;

1-[({cis-3-[methyl(7H-pyrrolo[2,3-d]pyrimidin-4-yl)amino] cyclobutyl}methyl)sulfonyl]-4-(trifluoromethyl)piperi-din-4-ol;

N-(cis-3-{[(4,4-difluoropiperidin-1-yl)sulfonyl] methyl}cyclobutyl)-N-methyl-7H-pyrrolo[2,3-d]pyrimi-din-4-amine;

(3S)-1-[({cis-3-[methyl(7H-pyrrolo[2,3-d]pyrimidin-4-yl) amino]cyclobutyl}meth-yl)sulfonyl]pyrrolidine-3-carbo-nitrile;

N-(cis-3-{[(3-chloro-4-fluorophenyl)sulfonyl]
methyl}cyclobutyl)-N-methyl-7H-pyrrolo[2,3-d]pyrimi-
din-4-amine;

N-(cis-3-{[(2-cyclopropylethyl)sulfonyl]
methyl}cyclobutyl)-N-methyl-7H-pyrrolo[2,3-d]pyrimi-
din-4-amine;

N-methyl-N-[cis-3-({[1-(propan-2-yl)pyrrolidin-3-yl]
sulfonyl}methyl)cyclobutyl]-7H-pyrrolo[2,3-d]pyrimi-
din-4-amine;

3,3-difluoro-N-{cis-3-[methyl(7H-pyrrolo[2,3-d]pyrimidin-
4-yl)amino]cyclobutyl}cyclobutane-sulfonamide;

1-[3-(cyanomethyl)oxetan-3-yl]-N-{cis-3-[methyl(7H-pyr-
rolo[2,3-d]pyrimidin-4-yl)amino]cyclobutyl}-methane-
sulfonamide;

cis-3-(cyanomethyl)-3-methyl-N-{cis-3-[methyl(7H-pyr-
rolo[2,3-d]pyrimidin-4-yl)amino]cyclobutyl}-cyclobu-
tanesulfonamide;

trans-3-(cyanomethyl)-3-methyl-N-{cis-3-[methyl(7H-pyr-
rolo[2,3-d]pyrimidin-4-yl)amino]
cyclobutyl}cyclobutanesulfonamide;

N-(2-cyanoethyl)-N-methyl-N'-{cis-3-[methyl(7H-pyrrolo
[2,3-d]pyrimidin-4-yl)amino]cyclobutyl}sulfuric
diamide;

N-{(1S,3R)-3-[methyl(7H-pyrrolo[2,3-d]pyrimidin-4-yl)
amino]cyclopentyl}propane-1-sulfonamide;

3-(2-hydroxypropan-2-yl)-N-{cis-3-[methyl(7H-pyrrolo[2,
3-d]pyrimidin-4-yl)amino]cyclobutyl}benzene-sulfona-
mide;

N-(cyclopropylmethyl)-N'-{cis-3-[methyl(7H-pyrrolo[2,3-
d]pyrimidin-4-yl)amino]cyclobutyl}sulfuric diamide;

N-{cis-3-[methyl(7H-pyrrolo[2,3-d]pyrimidin-4-yl)amino]
cyclobutyl}-4-(1H-pyrazol-3-yl)piperidine-1-sulfona-
mide;

2-methyl-N-{cis-3-[methyl(7H-pyrrolo[2,3-d]pyrimidin-4-
yl)amino]cyclobutyl}-2,6-dihydropyrrolo[3,4-c]pyra-
zole-5 (4H)-sulfonamide;

N-cyclopropyl-1-{trans-3-[methyl(7H-pyrrolo[2,3-d]py-
rimidin-4-yl)amino]cyclobutyl}methane-sulfonamide;

2-[({cis-3-[methyl(7H-pyrrolo[2,3-d]pyrimidin-4-yl)amino]
cyclobutyl}methyl)sulfonyl]pyridine-4-carbonitrile;

(1S,3S)-3-[({cis-3-[methyl(7H-pyrrolo[2,3-d]pyrimidin-4-
yl)amino]cyclobutyl}methyl)-sulfonyl]cyclopentanecar-
bonitrile;

(1R,3R)-3-[({cis-3-[methyl(7H-pyrrolo[2,3-d]pyrimidin-4-
yl)amino]cyclobutyl}methyl)sulfonyl]cyclopentanecar-
bonitrile;

1-cyclopropyl-N-{trans-3-[methyl(7H-pyrrolo[2,3-d]py-
rimidin-4-yl)amino]cyclobutyl}methane sulfonamide;

3-cyano-N-{trans-3-[methyl(7H-pyrrolo[2,3-d]pyrimidin-4-
yl)amino]cyclobutyl}pyrrolidine-1-sulfonamide;

N-methyl-N-{trans-3-[(propylsulfonyl)methyl]cyclobutyl}-
7H-pyrrolo[2,3-d]pyrimidin-4-amine; and, 2-methyl-N-{cis-3-[methyl(7H-pyrrolo[2,3-d]pyrimidin-4-
yl)amino]cyclobutyl}-1,3-thiazole-5-sulfonamide; or, a
pharmaceutically acceptable salt thereof.

The invention also provides said method, wherein the
compound is N-{cis-3-[methyl(7H-pyrrolo[2,3-d]pyrimi-
din-4-yl)amino]cyclobutyl}-propane-1-sulfonamide, or a
pharmaceutically acceptable salt thereof.

The invention further provides a method for treating
hidradenitis suppurtiva in a subject having lesions associated
with hidradenitis suppurativa, the method comprising the
step of administering to the subject in need thereof, a
compound selected from the group consisting of:

(1r,3r)-3-(4-(6-(3-amino-1-methyl-1H-pyrazol-4-yl)pyra-
zolo[1,5-a]pyrazin-4-yl)-1H-pyrazol-1-yl)-3-(cyanom-
ethyl)cyclobutane-1-carbonitrile;

2,2'-(3-(4-(6-(1-methyl-1H-pyrazol-4-yl)pyrazolo[1,5-a]
pyrazin-4-yl)-1H-pyrazol-1-yl)azetidine-1,3-diyl)diac-
etonitrile;

2-((1s,3r)-1-(4-(6-(5-(hydroxymethyl)-1H-pyrazol-3-yl)
pyrazolo[1,5-a]pyrazin-4-yl)-1H-pyrazol-1-yl)-3-
methoxycyclobutyl)acetonitrile;

5-(4-(1-((1s,3r)-1-(cyanomethyl)-3-methoxycyclobutyl)-
1H-pyrazol-4-yl)pyrazolo[1,5-a]pyrazin-6-yl)-1H-pyra-
zole-3-carboxamide;

(1s,3s)-3-(cyanomethyl)-3-(4-(6-(5-(hydroxymethyl)isoxa-
zol-3-yl)pyrazolo[1,5-a]pyrazin-4-yl)-1H-pyrazol-1-yl)
cyclobutane-1-carbonitrile;

(1r,3r)-3-(cyanomethyl)-3-(4-(6-(1-methyl-1H-pyrazol-4-
yl)pyrazolo[1,5-a]pyrazin-4-yl)-1H-pyrazol-1-yl)cy-
clobutane-1-carbonitrile;

(1s,3s)-3-(cyanomethyl)-3-(4-(6-(1-methyl-1H-pyrazol-4-
yl)pyrazolo[1,5-a]pyrazin-4-yl)-1H-pyrazol-1-yl)cy-
clobutane-1-carbonitrile;

(1r,3r)-3-(cyanomethyl)-3-(4-(3-methyl-6-(1-methyl-1H-
pyrazol-4-yl)pyrazolo[1,5-a]pyrazin-4-yl)-1H-pyrazol-1-
yl)cyclobutane-1-carbonitrile;

2-((1r,3s)-1-(4-(6-(3-amino-1H-pyrazol-5-yl)pyrazolo[1,5-
a]pyrazin-4-yl)-1H-pyrazol-1-yl)-3-methoxycyclobutyl)
acetonitrile;

2-(1-ethyl-3-(4-(6-(5-(hydroxymethyl)-1H-pyrazol-3-yl)
pyrazolo[1,5-a]pyrazin-4-yl)-1H-pyrazol-1-yl)azetidin-3-
yl)acetonitrile;

(1r,3r)-3-(cyanomethyl)-3-(4-(6-(1-methyl-3-oxo-2,3-di-
hydro-1H-pyrazol-4-yl)pyrazolo[1,5-a]pyrazin-4-yl)-1H-
pyrazol-1-yl)cyclobutane-1-carbonitrile (trans isomer);

(1r,3r)-3-(cyanomethyl)-3-(4-(6-(1-(hydroxymethyl)-1H-
pyrazol-4-yl)pyrazolo[1,5-a]pyrazin-4-yl)-1H-pyrazol-1-
yl)cyclobutane-1-carbonitrile; and, or, a pharmaceutically acceptable salt thereof.

The invention also provides said method, wherein the
compound is (1r,3r)-3-(cyanomethyl)-3-(4-(6-(1-methyl-
1H-pyrazol-4-yl)pyrazolo[1,5-a]pyrazin-4-yl)-1H-pyrazol-
1-yl)cyclobutane-1-carbonitrile, or a pharmaceutically
acceptable salt thereof.

The invention also provides said method, wherein the
compound is (1s,3s)-3-(cyanomethyl)-3-(4-(6-(1-methyl-
1H-pyrazol-4-yl)pyrazolo[1,5-a]pyrazin-4-yl)-1H-pyrazol-
1-yl)cyclobutane-1-carbonitrile, or a pharmaceutically
acceptable salt thereof.

The invention also provides said method, wherein the
subject's HiSCR score is improved after administration of
the compound.

The invention also provides said method, wherein the
median size of the subject's hidradenitis suppurativa lesions
is reduced after administration of the pharmaceutical com-
position.

The invention also provides said method, wherein the
subject's pain associated with the subject's hidradenitis
suppurativa lesions is reduced after administration of the
compound.

The invention also provides said method, wherein the
subject's time to develop new hidradenitis suppurativa
lesions is increased after administration of the compound.

The invention further provides a pharmaceutical or a
veterinary composition comprising any compound set forth
above, or a pharmaceutically acceptable salt thereof, and a
pharmaceutically acceptable carrier, for use in the treatment
and prevention of hidradenitis suppurtiva.

The invention also provides a method for treating
hidradenitis suppurtiva in a subject having lesions associated
with hidradenitis suppurativa, the method comprising the
step of administering to the subject in need thereof, a compound which inhibits JAK1, Tyk2/JAK1 or Tyk2 in an amount effective to treat a symptom of hidradenitis suppurativa in the subject.

The invention also provides the method, wherein said effective amount is about 0.01 to about 100 mg/kg of body weight/day, or more preferably about 0.1 to about 10.0 mg/kg, in a single dose or as divided doses administered two, three or four times per day.

The invention also provides a method for treating hidradenitis suppurtiva in a subject having lesions associated with hidradenitis suppurativa, the method comprising the step of administering to the subject in need thereof, N-{cis-3-[methyl(7H-pyrrolo[2,3-d]pyrimidin-4-yl)amino]cyclobutyl}-propane-1-sulfonamide, or a pharmaceutically acceptable salt thereof, in an amount effective to treat a symptom of hidradenitis suppurativa in the subject.

The invention also provides the method, wherein said effective amount is about 0.01 to about 100 mg/kg of body weight/day, or more preferably about 0.1 to about 10.0 mg/kg, in a single dose or as divided doses administered two, three or four times per day.

The invention also provides a method for treating hidradenitis suppurtiva in a subject having lesions associated with hidradenitis suppurativa, the method comprising the step of administering to the subject in need thereof, [(1S)-2,2-difluorocyclo-propyl][(1R,5S)-3-{2-[(1-methyl-1H-pyrazol-4-yl)amino]pyrimidin-4-yl}-3,8-diazabicyclo[3.2.1]oct-8-yl]methanone or a pharmaceutically acceptable salt thereof, in an amount effective to treat a symptom of hidradenitis suppurativa in the subject.

The invention also provides the method, wherein said effective amount is about 0.01 to about 100 mg/kg of body weight/day, or more preferably about 0.1 to about 10.0 mg/kg, in a single dose or as divided doses administered two, three or four times per day. The invention also provides the method, wherein said effective amount is about 45 mg administered QD.

The invention also provides the method, wherein the salt is the p-toluenesulfonic acid salt.

The invention also provides a method for treating hidradenitis suppurtiva in a subject having lesions associated with hidradenitis suppurativa, the method comprising the step of administering to the subject in need thereof, (1r,3r)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile or a pharmaceutically acceptable salt thereof, in an amount effective to treat a symptom of hidradenitis suppurativa in the subject.

The invention also provides the method, wherein said effective amount is about 0.01 to about 100 mg/kg of body weight/day, or more preferably about 0.1 to about 10.0 mg/kg, in a single dose or as divided doses administered two, three or four times per day. The invention also provides the method, wherein said effective amount is about 400 mg administered QD.

In therapeutic use for treating disorders in a mammal, a compound of the present invention or its pharmaceutical compositions can be administered orally, parenterally, topically, rectally, transmucosally, or intestinally. Parenteral administrations include indirect injections to generate a systemic effect or direct injections to the afflicted area. Topical administrations include the treatment of skin or organs readily accessible by local application, for example, eyes or ears. It also includes transdermal delivery to generate a systemic effect. The rectal administration includes the form of suppositories. The preferred routes of administration are oral, topical and parenteral.

Pharmaceutical compositions of the present invention may be manufactured by methods well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in a conventional manner using one or more pharmaceutically acceptable carriers comprising excipients and auxiliaries, which facilitate processing of the active compound into preparations, which can be used pharmaceutically. Proper formulation is dependent upon the route of administration chosen. Pharmaceutically acceptable excipients and carriers are generally known to those skilled in the art and are thus included in the instant invention. Such excipients and carriers are described, for example, in *Remington's Pharmaceutical Sciences*, Mack Pub. Co., New Jersey (1991). The formulations of the invention can be designed to be short-acting, fast-releasing, long-acting, and sustained-releasing. Thus, the pharmaceutical formulations can also be formulated for controlled release or for slow release.

Pharmaceutical compositions suitable for use in the present invention include compositions wherein the active ingredients are contained in an amount sufficient to achieve the intended purpose, i.e., control or the treatment of HS. More specifically, a therapeutically effective amount means an amount of compound effective to prevent, alleviate or ameliorate symptoms/signs of the disease or prolong the survival of the subject being treated.

The quantity of active component, which is the compound of this invention, in the pharmaceutical composition and unit dosage form thereof, may be varied or adjusted widely depending upon the manner of administration, the potency of the particular compound and the desired concentration. Determination of a therapeutically effective amount is well within the capability of those skilled in the art. Generally, the quantity of active component will range between 0.01% to 99% by weight of the composition.

Generally, a therapeutically effective amount of dosage of active component will be in the range of about 0.01 to about 100 mg/kg of body weight/day, preferably about 0.1 to about 10 mg/kg of body weight/day, more preferably about 0.3 to 3 mg/kg of body weight/day, even more preferably about 0.3 to 1.5 mg/kg of body weight/day It is to be understood that the dosages may vary depending upon the requirements of each subject and the severity of the disorders or diseases being treated.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

Suitable agents for use in combination therapy with a compound set forth herein, or a pharmaceutically acceptable salt thereof, or pharmaceutically acceptable solvate of said compound or salt, particularly in the treatment of the disease, include: a 5-lipoxygenase activating protein (FLAP) antagonist; a leukotriene antagonist (LTRA) such as an antagonist of $LTB_4$, $LTC_4$, $LTD_4$, $LTE_4$, $CysLT_1$ or $CysLT_2$, e.g., montelukast or zafirlukast; a histamine receptor antagonist, such as a histamine type 1 receptor antagonist or a histamine type 2 receptor antagonist, e.g., loratidine, fexofenadine, desloratidine, levocetirizine, methapyrilene or cetirizine; an α1-adrenoceptor agonist or an α2-adrenoceptor agonist, e.g., phenylephrine, methoxamine, oxymetazoline or methylnorephrine; a muscarinic M3 receptor antagonist, e.g. tiotropium or ipratropium; a dual muscarinic M3 receptor antagononist/β2 agonist; a PDE inhibitor, such as a PDE3 inhibitor, a PDE4 inhibitor or a PDE5 inhibitor, e.g., theophylline, sildenafil, vardenafil, tadalafil, ibudilast, cilomilast or roflumilast; sodium cromoglycate or sodium nedocromil; a cyclooxygenase (COX) inhibitor, such as a non-selective inhibitor (e.g., aspirin or ibuprofen) or a selective inhibitor (e.g. celecoxib or valdecoxib); a glucocorticosteroid, e.g., fluticasone, mometasone, dexamethasone, prednisolone, budesonide, ciclesonide or beclamethasone; an anti-inflammatory monoclonal antibody, e.g., infliximab, adalimumab, tanezumab, ranibizumab, bevacizumab or mepolizumab; a β2 agonist, e.g., salmeterol, albuterol, salbutamol, fenoterol or formoterol, particularly a long-acting β2 agonist; an intigrin antagonist, e.g., natalizumab; an adhesion molecule inhibitor, such as a VLA-4 antagonist; a kinin $B_1$ or $B_2$ receptor antagonist; an immunosuppressive agent, such as an inhibitor of the IgE pathway (e.g., omalizumab) or cyclosporine; a matrix metalloprotease (MMP) inhibitor, such as an inhibitor of MMP-9 or MMP-12; a tachykinin $NK_1$, $NK_2$ or $NK_3$ receptor antagonist; a protease inhibitor, such as an inhibitor of elastase, chymase or catheopsin G; an adenosine $A_{2a}$ receptor agonist; an adenosine $A_{2b}$ receptor antagonist; a urokinase inhibitor; a dopamine receptor agonist (e.g., ropinirole), particularly a dopamine D2 receptor agonist (e.g., bromocriptine); a modulator of the NFκB pathway, such as an IKK inhibitor; a further modulator of a cytokine signalling pathway such as an inhibitor of syk kinase, p38 kinase, SPHK-1 kinase, Rho kinase, EGF-R or MK-2; a mucolytic, mucokinetic or anti-tussive agent; an antibiotic; an antiviral agent; a vaccine; a chemokine; an epithelial sodium channel (ENaC) blocker or Epithelial sodium channel (ENaC) inhibitor; a nucleotide receptor agonist, such as a P2Y2 agonist; a thromboxane inhibitor; niacin; a 5-lipoxygenase (5-LO) inhibitor, e.g., Zileuton; an adhesion factor, such as VLAM, ICAM or ELAM; a CRTH2 receptor ($DP_2$) antagonist; a prostaglandin $D_2$ receptor ($DP_1$) antagonist; a haematopoietic prostaglandin D2 synthase (HPGDS) inhibitor; interferon-β; a soluble human TNF receptor, e.g., Etanercept; a HDAC inhibitor; a phosphoinositotide 3-kinase gamma (PI3Kγ) inhibitor; a phosphoinositide 3-kinase delta (PI3Kδ) inhibitor; a CXCR-1 or a CXCR-2 receptor antagonist; an IRAK-4 inhibitor; and, a TLR-4 or TLR-9 inhibitor, including the pharmaceutically acceptable salts of the specifically named compounds and the pharmaceutically acceptable solvates of said specifically named compounds and salts.

Chemical Synthesis

The compounds of the invention may be prepared by any method known in the art. In particular, the compounds of the invention can be prepared by the procedures described by reference to the prior art references in which they are disclosed.

For those compounds which inhibit JAK1 specifically, including N-{cis-3-[methyl(7H-pyrrolo[2,3-d]pyrimidin-4-yl)amino]cyclobutyl}-propane-1-sulfonamide, preparative methods are disclosed in U.S. Pat. No. 9,035,074, the contents of which are incorporated herein in their entirety.

For those compounds which inhibit Tyk2/JAK1 specifically, including [(1S)-2,2-difluorocyclo-propyl][(1R,5S)-3-{2-[(1-methyl-1H-pyrazol-4-yl)amino]pyrimidin-4-yl}-3,8-diazabicyclo[3.2.1]oct-8-yl]methanone, preparative methods are disclosed in U.S. Pat. No. 9,663,526, the contents of which are incorporated herein in their entirety.

For those compounds which inhibit Tyk2 specifically, including (1r,3r)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, preparative methods are disclosed in U.S. Pat. No. 10,144,738, the contents of which are incorporated herein in their entirety.

EXAMPLES

The following non-limiting examples are presented merely to illustrate the present invention. The skilled person will understand that there are numerous equivalents and variations not exemplified but which still form part of the present teachings.

Example 1

Hidradenitis Suppurativa Clinical Response (HiSCR)

This study is being conducted to provide data on efficacy, safety, tolerability and pharmacokinetics of the therapeutic agent being examined in the oral treatment of moderate to severe HS. The study will have a maximum duration of approximately 26 weeks. This includes an up-to-6-week Screening Period, a 16-week Dosing Period and a 4-week Follow-up Period. The study will enroll a total of approximately 192 participants (expected to provide approximately 156 completers). Following the screening period, participants who meet eligibility criteria at the baseline visit, will be randomly assigned to receive 1 of 6 treatments. One oral dose level of each therapeutic agent [(1S)-2,2-difluorocyclo-propyl][(1R,5S)-3-{2-[(1-methyl-1H-pyrazol-4-yl)amino]pyrimidin-4-yl}-3,8-diazabicyclo[3.2.1]oct-8-yl]methanone (45 mg QD) and (1r,3r)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile (400 mg QD) or matching placebo in a 3:1 ratio will be investigated. For analysis, placebo groups will be combined to yield final IP:placebo ratio of 1:1:1:1 for each IP and placebo. No more than 30% of enrolled participants will be inadequate anti-TNF responders. Participants will be stratified according to whether they are an inadequate anti-TNF responder or not.

Additionally, no more than 20% of enrolled participants may enter the study on a background of concomitant oral antibiotic therapy for treatment of HS; the dosing regimen (dose and frequency) must have been stable for at least 8 weeks (56 days) prior to the baseline (Day 1) visit and must remain stable throughout study participation. Antibiotics taken on an "as needed" (PRN) basis are not considered a stable dose. Participants will be stratified according to whether they are on a background of concomitant antibiotic therapy or not. The chronic toxicology package for each asset supports the planned study treatment duration of 16 weeks. Hidradenitis suppurative clinical response, the primary endpoint used, is defined as:

At least a 50% reduction in the total abscess and inflammatory nodule (AN) count relative to baseline, and no increase in abscess count, and no increase in draining fistula count.

Example 2

Lesion Counts

The number of inflammatory and non-inflammatory nodules, abscesses, draining and non-draining fistulas, and hypertrophic scars, as well as the physical location (right/left axilla, right/left inframammary, intermammary, right/left buttock, right/left inguino-crural fold, perianal, perineal, other) will be assessed according to the standard of the art.

Example 3

Abscess Count

Number of abscesses (fluctuant, with or without drainage, tender or painful) will be counted in each of the regions as defined above.

Example 4

Inflammatory Nodule Count

Number of inflammatory nodules (tender, erythematous, pyogenic granuloma lesion) will be counted in each of the regions as defined above.

Example 5

Fistula Count

Number of fistula (sinus tracts, with communications to skin surface, draining purulent fluid) will be counted in each of the regions as defined above.

Example 6

Hurley Staging

Hurley staging is defined as follows:

Stage I: Abscess formation, single or multiple, without sinus tracts and cicatrization (scarring).

Stage II: One or more widely separated recurrent abscesses with tract formation and cicatrization (scars).

Stage III: Multiple interconnected tracts and abscesses across the entire area, with diffuse or near diffuse involvement.

Hurley staging will be performed according to the standard of the art.

Example 7

Modified Sartorius Scale

The Modified Sartorius score is calculated by counting lesions in the following 12 anatomic regions: left axilla, right axilla, left sub/inframammary area, right sub/inframammary area, intermammary area, left buttock, right buttock, left inguino-crural fold, right inguino-crural fold, perianal area, perineal area, other. For each anatomic region, calculate the regional Sartorius score as follows:

Anatomic region involved: 3 points per region involved (i.e., any lesion count in this anatomic region >0; otherwise 0 points).

Number and scores of lesions (abscesses, nodules, fistulas, scars): 2 points for each nodule (inflammatory and non-inflammatory), 4 points for each abscess, 4 points for each fistula (draining and non-draining), 1 point for each hypertrophic scar, 1 point for each "other".

Longest distance between 2 relative lesions (i.e., 0 if no active lesion; 2 if longest distance between 2 relevant lesions or size <50 mm; 4 if longest distance between 2 relevant lesions or size ≥50 mm and <100 mm; 6 if longest distance between 2 relevant lesions or size ≥100 mm. Lesions clearly separated by normal skin in each region: If all lesions clearly separated by normal appearing skin, 0 points; 6 points if otherwise.

The total Modified Sartorius score is the sum of all of the 12 regional scores.

Example 8

Erythema Assessment

The overall degree of erythema will be assessed for each anatomic region affected by HS using a four-point ordinal scale ranging between 0 (no redness), 1 (faint but discernible pink coloration), 2 (moderate red coloration), or 3 (very red or bright red coloration).

What is claimed is:

1. A method for treating hidradenitis suppurativa in a subject having lesions associated with hidradenitis suppurativa, the method comprising the step of administering to the subject in need thereof a JAK inhibitor selected from the group consisting of [(1S)-2,2-difluorocyclo-propyl][(1R,5S)-3-{2-[(1-methyl-1H-pyrazol-4-yl)amino]pyrimidin-4-yl}-3,8-diazabicyclo[3.2.1]oct-8-yl]methanone, [(1R)-2,2-difluorocyclo-propyl][(1R,5S)-3-{2-[(1-methyl-1H-pyrazol-4-yl)amino]pyrimidin-4-yl}-3,8-diazabicyclo[3.2.1]oct-8-yl]methanone, N-{cis-3-[methyl(7H-pyrrolo[2,3-d]pyrimidin-4-yl)amino]cyclobutyl}-propane-1-sulfonamide, (1r,3r)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, (1s,3s)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, or, a pharmaceutically acceptable salt thereof.

2. The method of claim 1, wherein said JAK inhibitor is [(1S)-2,2-difluorocyclo-propyl][(1R,5S)-3-{2-[(1-methyl-1H-pyrazol-4-yl)amino]pyrimidin-4-yl}-3,8-diazabicyclo[3.2.1]oct-8-yl]methanone; or, a pharmaceutically acceptable salt thereof.

3. The method of claim 1, wherein said JAK inhibitor is [(1R)-2,2-difluorocyclo-propyl][(1R,5S)-3-{2-[(1-methyl-1H-pyrazol-4-yl)amino]pyrimidin-4-yl}-3,8-diazabicyclo[3.2.1]oct-8-yl]methanone; or, a pharmaceutically acceptable salt thereof.

4. The method of claim 1, wherein said salt is the p-toluenesulfonic acid salt.

5. The method of claim 1, wherein said JAK inhibitor is N-{cis-3-[methyl(7H-pyrrolo[2,3-d]pyrimidin-4-yl)amino]cyclobutyl}-propane-1-sulfonamide, or a pharmaceutically acceptable salt thereof.

6. The method of claim 1, wherein said JAK inhibitor is (1r,3r)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, or a pharmaceutically acceptable salt thereof.

7. The method of claim 1, wherein said JAK inhibitor is (1s,3s)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, or a pharmaceutically acceptable salt thereof.

8. The method of claim 1, wherein the treatment reduces inflammatory nodules, abscess and draining fistulas as measured by the subject's hidradenitis suppurativa clinical response (HiSCR) score.

9. The method of claim 1, wherein the treatment reduces the median size of the subject's hidradenitis suppurativa lesions.

10. The method of claim 1, wherein the treatment reduces the subject's pain associated with the subject's hidradenitis suppurativa lesions.

11. The method of claim 1, wherein the treatment increases the subject's time to develop new hidradenitis suppurativa lesions.

12. The method of claim 1, comprising the step of administering to the subject in need thereof [(1S)-2,2-dif-luorocyclo-propyl][(1R,5S)-3-{2-[(1-methyl-1H-pyrazol-4-yl)amino]pyrimidin-4-yl}-3,8-diazabicyclo[3.2.1]oct-8-yl] methanone, or, a pharmaceutically acceptable salt thereof in an amount effective to treat a symptom of hidradenitis suppurativa in the subject.

13. The method of claim 12, wherein said effective amount is about 0.01 to about 100 mg/kg of body weight/ day, in a single dose or as divided doses administered two, three or four times per day.

14. A method for treating hidradenitis suppurativa in a human subject having lesions associated with hidradenitis suppurativa, the method comprising the step of administer-ing to the subject in need thereof N-{cis-3-[methyl(7H-pyrrolo[2,3-d]pyrimidin-4-yl)amino]cyclobutyl}-propane-1-sulfonamide, or a pharmaceutically acceptable salt thereof, in an amount effective to treat a symptom of hidradenitis suppurativa in the subject.

15. The method of claim 14, wherein said effective amount is about 0.01 to about 100 mg/kg of body weight/ day, in a single dose or as divided doses administered two, three or four times per day.

16. A method for treating hidradenitis suppurativa in a subject having lesions associated with hidradenitis suppu-rativa, the method comprising the step of administering to the subject in need thereof a JAK inhibitor selected from the group consisting of JAK1, Tyk2/JAK1, and Tyk2, wherein the treatment effectuates at least one of (i) a reduction of inflammatory nodules, abscess and draining fistulas as mea-sured by the subject's hidradenitis suppurativa clinical response (HiSCR) score, (ii) a reduction of the median size of the subject's hidradenitis suppurativa lesions, (iii) a reduction of the subject's pain associated with the subject's hidradenitis suppurativa lesions, (iv) and/or an increase of the subject's time to develop new hidradenitis suppurativa lesions.

17. The method of claim 16, wherein the JAK inhibitor is selected from the group consisting of [(1S)-2,2-difluorocy-clo-propyl][(1R,5S)-3-{2-[(1-methyl-1H-pyrazol-4-yl) amino]pyrimidin-4-yl}-3,8-diazabicyclo[3.2.1]oct-8-yl] methanone, [(1R)-2,2-difluorocyclo-propyl][(1R,5S)-3-{2-[(1-methyl-1H-pyrazol-4-yl)amino]pyrimidin-4-yl}-3,8-diazabicyclo[3.2.1]oct-8-yl]methanone, N-{cis-3-[methyl (7H-pyrrolo[2,3-d]pyrimidin-4-yl)amino]cyclobutyl}-propane-1-sulfonamide, (1r,3r)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, (1s,3s)-3-(cyanomethyl)-3-(4-(6-(1-methyl-1H-pyrazol-4-yl)pyrazolo [1,5-a]pyrazin-4-yl)-1H-pyrazol-1-yl)cyclobutane-1-carbonitrile, or, a pharmaceutically acceptable salt thereof.

18. The method of claim 16, wherein the JAK inhibitor is [(1S)-2,2-difluorocyclo-propyl][(1R,5S)-3-{2-[(1-methyl-1H-pyrazol-4-yl)amino]pyrimidin-4-yl}-3,8-diazabicyclo [3.2.1]oct-8-yl]methanone; or, a pharmaceutically accept-able salt thereof.

* * * * *